(12) United States Patent
Chow

(10) Patent No.: US 7,745,149 B2
(45) Date of Patent: Jun. 29, 2010

(54) TUMOR MARKERS FOR OVARIAN CANCER DIAGNOSIS

(75) Inventor: Song-Nan Chow, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 12/326,369

(22) Filed: Dec. 2, 2008

(65) Prior Publication Data

US 2009/0098595 A1     Apr. 16, 2009

Related U.S. Application Data

(63) Continuation-in-part of application No. 11/532,079, filed on Sep. 14, 2006, now abandoned.

(51) Int. Cl.
  *G01N 33/53*    (2006.01)
(52) U.S. Cl. ........................... 435/7.1; 530/350
(58) Field of Classification Search ................. 435/7.1; 530/350
See application file for complete search history.

(56) References Cited

OTHER PUBLICATIONS

Brule et al (Lab. Inv., 83(3):377-386, 2003).*
Siewinski et al (Bio. Chem., 384:1103-1107, 2003).*

* cited by examiner

*Primary Examiner*—Stephen L Rawlings
*Assistant Examiner*—Brad Duffy
(74) *Attorney, Agent, or Firm*—WPAT, P.C.; Anthony King

(57) ABSTRACT

The present invention relates to a tumor marker for diagnosis of ovarian cancer, which is selected from the group consisting of galectin-1, cathepsin B, MHC class I antigen, heat shock protein (HSP) 27, ubiquitin carboxy-termal esterase L1, plasma retinol-binding protein (PRBP), transthyretin, SH3 binding glutamate-rich protein, tubulin-specific chaperone A, RNA binding protein regulatory subunit, γ-actin, tropomyosin and calcium/calmodulin-stimulated cyclic nucleotide phosphatase. The ovarian cancer is diagnosed effectively and efficiently based on detecting the expression levels of the tumor markers in the invention from the ovarian tissue sample of an individual to be diagnosed.

6 Claims, 1 Drawing Sheet

SEQUENCE LISTING

<160> NUMBER OF SEQ ID NOS: 13

<210> SEQ ID NO 1
<211> LENGTH: 135
<212> TYPE: PRT
<213> ORGANISM: Homo sapiens

<400> SEQUENCE: 1

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

```
Leu Asn Leu Gly Lys Asp Ser Asn Asn Leu Cys Leu His Phe Asn Pro
            35                  40                  45

Arg Phe Asn Ala His Gly Asp Ala Asn Thr Ile Val Cys Asn Ser Lys
        50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
            130                 135

<210> SEQ ID NO 2
<211> LENGTH: 153
<212> TYPE: PRT
<213> ORGANISM: Homo sapiens

<400> SEQUENCE: 2

Cys Glu His His Val Asn Gly Ser Arg Pro Pro Cys Thr Gly Glu Gly
1               5                   10                  15

Asp Thr Pro Lys Cys Ser Lys Ile Cys Glu Pro Gly Tyr Ser Pro Thr
            20                  25                  30

Tyr Lys Gln Asp Lys His Tyr Gly Tyr Asn Ser Tyr Ser Val Ser Asn
        35                  40                  45

Ser Glu Lys Asp Ile Met Ala Glu Ile Tyr Lys Asn Gly Pro Val Glu
    50                  55                  60

Gly Ala Phe Ser Val Tyr Ser Asp Phe Leu Leu Tyr Lys Ser Gly Val
65                  70                  75                  80

Tyr Gln His Val Thr Gly Glu Met Met Gly His Ala Ile Arg Ile
                85                  90                  95

Leu Gly Trp Gly Val Glu Asn Gly Thr Pro Tyr Trp Leu Val Ala Asn
            100                 105                 110

Ser Trp Asn Thr Asp Trp Gly Asp Asn Gly Phe Phe Lys Ile Leu Arg
        115                 120                 125

Gly Gln Asp His Cys Gly Ile Glu Ser Glu Val Val Ala Gly Ile Pro
    130                 135                 140

Arg Thr Asp Gln Tyr Trp Glu Lys Ile
145                 150

<210> SEQ ID NO 3
<211> LENGTH: 181
<212> TYPE: PRT
<213> ORGANISM: Homo sapiens

<400> SEQUENCE: 3

Ser His Ser Met Arg Tyr Phe Tyr Thr Ala Val Ser Arg Pro Gly Arg
1               5                   10                  15

Gly Glu Pro His Phe Ile Ala Val Gly Tyr Val Asp Asp Thr Gln Phe
            20                  25                  30

Val Arg Phe Asp Ser Asp Ala Ala Ser Pro Arg Gly Glu Pro Arg Glu
        35                  40                  45

Pro Trp Val Glu Gln Glu Gly Pro Glu Tyr Trp Asp Arg Glu Thr Gln
    50                  55                  60
```

```
Lys Tyr Lys Arg Gln Ala Gln Ala Asp Arg Val Asn Leu Arg Lys Leu
 65                  70                  75                  80

Arg Gly Tyr Tyr Asn Gln Ser Glu Asp Gly Ser His Thr Leu Gln Arg
                 85                  90                  95

Met Phe Gly Cys Asp Leu Gly Pro Asp Gly Arg Leu Leu Arg Gly Tyr
            100                 105                 110

Asn Gln Phe Ala Tyr Asp Gly Lys Asp Tyr Ile Ala Leu Asn Glu Asp
        115                 120                 125

Leu Arg Ser Trp Thr Ala Ala Asp Thr Ala Ala Gln Ile Thr Gln Arg
    130                 135                 140

Lys Trp Glu Ala Ala Arg Glu Ala Glu Gln Arg Arg Ala Tyr Leu Glu
145                 150                 155                 160

Gly Thr Cys Val Glu Trp Leu Arg Arg Tyr Leu Glu Asn Gly Lys Glu
            165                 170                 175

Thr Leu Gln Arg Ala
        180

<210> SEQ ID NO 4
<211> LENGTH: 205
<212> TYPE: PRT
<213> ORGANISM: Homo sapiens

<400> SEQUENCE: 4

Met Thr Glu Arg Arg Val Pro Phe Ser Leu Leu Arg Gly Pro Ser Trp
 1               5                  10                  15

Asp Pro Phe Arg Asp Trp Tyr Pro His Ser Arg Leu Phe Asp Gln Ala
                 20                  25                  30

Phe Gly Leu Pro Arg Leu Pro Glu Glu Trp Ser Gln Trp Leu Gly Gly
            35                  40                  45

Ser Ser Trp Pro Gly Tyr Val Arg Pro Leu Pro Pro Ala Ala Ile Glu
        50                  55                  60

Ser Pro Ala Val Ala Ala Pro Ala Tyr Ser Arg Ala Leu Ser Arg Gln
 65                  70                  75                  80

Leu Ser Ser Gly Val Ser Glu Ile Arg His Thr Ala Asp Arg Trp Arg
                 85                  90                  95

Val Ser Leu Asp Val Asn His Phe Ala Pro Asp Glu Leu Thr Val Lys
            100                 105                 110

Thr Lys Asp Gly Val Val Glu Ile Thr Gly Lys His Glu Glu Arg Gln
        115                 120                 125

Asp Glu His Gly Tyr Ile Ser Arg Cys Phe Thr Arg Lys Tyr Thr Leu
    130                 135                 140

Pro Pro Gly Val Asp Pro Thr Gln Val Ser Ser Ser Leu Ser Pro Glu
145                 150                 155                 160

Gly Thr Leu Thr Val Glu Ala Pro Met Pro Lys Leu Ala Thr Gln Ser
            165                 170                 175

Asn Glu Ile Thr Ile Pro Val Thr Phe Glu Ser Arg Ala Gln Leu Gly
        180                 185                 190

Gly Pro Glu Ala Ala Lys Ser Asp Glu Thr Ala Ala Lys
    195                 200                 205

<210> SEQ ID NO 5
<211> LENGTH: 223
<212> TYPE: PRT
<213> ORGANISM: Homo sapiens

<400> SEQUENCE: 5
```

```
Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
                35                  40                  45

Leu Leu Leu Leu Phe Pro Leu Thr Ala Gln His Glu Asn Phe Arg Lys
50                      55                  60

Lys Gln Ile Glu Glu Leu Lys Gly Gln Glu Val Ser Pro Lys Val Tyr
65                  70                  75                  80

Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
                100                 105                 110

Val Leu Lys Gln Phe Leu Ser Glu Thr Glu Lys Met Ser Pro Glu Asp
            115                 120                 125

Arg Ala Lys Cys Phe Glu Lys Asn Glu Ala Ile Gln Ala Ala His Asp
        130                 135                 140

Ala Val Ala Gln Glu Gly Gln Cys Arg Val Asp Asp Lys Val Asn Phe
145                 150                 155                 160

His Phe Ile Leu Phe Asn Asn Val Asp Gly His Leu Tyr Glu Leu Asp
                165                 170                 175

Gly Arg Met Pro Phe Pro Val Asn His Gly Ala Ser Ser Glu Asp Thr
            180                 185                 190

Leu Leu Lys Asp Ala Ala Lys Val Cys Arg Glu Phe Thr Glu Arg Glu
        195                 200                 205

Gln Gly Glu Val Arg Phe Ser Ala Val Ala Leu Cys Lys Ala Ala
210                 215                 220

<210> SEQ ID NO 6
<211> LENGTH: 201
<212> TYPE: PRT
<213> ORGANISM: Homo sapiens

<400> SEQUENCE: 6

Met Lys Trp Val Trp Ala Leu Phe Leu Leu Ala Ala Leu Gly Ser Gly
1               5                   10                  15

Arg Ala Glu Arg Asp Cys Arg Val Ser Ser Phe Arg Val Lys Glu Asn
            20                  25                  30

Phe Asp Lys Ala Arg Phe Ser Gly Thr Trp Tyr Ala Met Ala Lys Lys
        35                  40                  45

Asp Pro Glu Gly Leu Phe Leu Gln Asp Asn Ile Val Ala Glu Phe Ser
50                  55                  60

Val Asp Glu Thr Gly Gln Met Ser Ala Thr Ala Lys Gly Arg Val Arg
65                  70                  75                  80

Leu Leu Asn Asn Trp Asp Val Cys Ala Asp Met Val Gly Thr Phe Thr
                85                  90                  95

Asp Thr Glu Asp Pro Ala Lys Phe Lys Met Lys Tyr Trp Gly Val Ala
            100                 105                 110

Ser Phe Leu Gln Lys Gly Asn Asp Asp His Trp Ile Val Asp Thr Asp
        115                 120                 125

Tyr Asp Thr Tyr Ala Val Gln Tyr Ser Cys Arg Leu Leu Asn Leu Asp
130                 135                 140

Gly Thr Cys Ala Asp Ser Tyr Ser Phe Val Phe Ser Arg Asp Pro Asn
145                 150                 155                 160
```

Gly Leu Pro Pro Glu Ala Gln Lys Ile Val Arg Gln Arg Gln Glu Glu
                165                 170                 175

Leu Cys Leu Ala Arg Gln Tyr Arg Leu Ile Val His Asn Gly Tyr Cys
            180                 185                 190

Asp Gly Arg Ser Glu Arg Asn Leu Leu
        195                 200

<210> SEQ ID NO 7
<211> LENGTH: 147
<212> TYPE: PRT
<213> ORGANISM: Homo sapiens

<400> SEQUENCE: 7

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145

<210> SEQ ID NO 8
<211> LENGTH: 114
<212> TYPE: PRT
<213> ORGANISM: Homo sapiens

<400> SEQUENCE: 8

Met Val Ile Arg Val Tyr Ile Ala Ser Ser Ser Gly Ser Thr Ala Ile
1               5                   10                  15

Lys Lys Lys Gln Gln Asp Val Leu Gly Phe Leu Glu Ala Asn Lys Ile
            20                  25                  30

Gly Phe Glu Glu Lys Asp Ile Ala Ala Asn Glu Glu Asn Arg Lys Trp
        35                  40                  45

Met Arg Glu Asn Val Pro Glu Asn Ser Arg Pro Ala Thr Gly Tyr Pro
50                  55                  60

Leu Pro Pro Gln Ile Phe Asn Glu Ser Gln Tyr Arg Gly Asp Tyr Asp
65                  70                  75                  80

Ala Phe Phe Glu Ala Arg Glu Asn Asn Ala Val Tyr Ala Phe Leu Gly
                85                  90                  95

Leu Thr Ala Pro Pro Gly Ser Lys Glu Ala Glu Val Gln Ala Lys Gln
            100                 105                 110

Gln Ala

<210> SEQ ID NO 9
<211> LENGTH: 108
<212> TYPE: PRT
<213> ORGANISM: Homo sapiens

<400> SEQUENCE: 9

```
Met Ala Asp Pro Arg Val Arg Gln Ile Lys Ile Lys Thr Gly Val Val
1               5                   10                  15

Lys Arg Leu Val Lys Glu Lys Val Met Tyr Glu Lys Glu Ala Lys Gln
                20                  25                  30

Gln Glu Glu Lys Ile Glu Lys Met Arg Ala Glu Asp Gly Glu Asn Tyr
            35                  40                  45

Asp Ile Lys Lys Gln Ala Glu Ile Leu Gln Glu Ser Arg Met Met Ile
        50                  55                  60

Pro Asp Cys Gln Arg Arg Leu Glu Ala Ala Tyr Leu Asp Leu Gln Arg
65                  70                  75                  80

Ile Leu Glu Asn Glu Lys Asp Leu Glu Ala Glu Glu Tyr Lys Glu
                85                  90                  95

Ala Arg Leu Val Leu Asp Ser Val Lys Leu Glu Ala
            100                 105
```

<210> SEQ ID NO 10
<211> LENGTH: 189
<212> TYPE: PRT
<213> ORGANISM: Homo sapiens

<400> SEQUENCE: 10

```
Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
                20                  25                  30

Val Thr Val Ala Gly Leu Ala Gly Lys Asp Pro Val Gln Cys Ser Arg
            35                  40                  45

Asp Val Val Ile Cys Pro Asp Ala Ser Leu Glu Asp Ala Lys Lys Glu
        50                  55                  60

Gly Pro Tyr Asp Val Val Leu Pro Gly Gly Asn Leu Gly Ala Gln
65                  70                  75                  80

Asn Leu Ser Glu Ser Ala Ala Val Lys Glu Ile Leu Lys Glu Gln Glu
                85                  90                  95

Asn Arg Lys Gly Leu Ile Ala Ala Ile Cys Ala Gly Pro Thr Ala Leu
            100                 105                 110

Leu Ala His Glu Ile Gly Phe Gly Ser Lys Val Thr Thr His Pro Leu
        115                 120                 125

Ala Lys Asp Lys Met Met Asn Gly Gly His Tyr Thr Tyr Ser Glu Asn
    130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Asn Gly Lys Glu
                165                 170                 175

Val Ala Ala Gln Val Lys Ala Pro Leu Val Leu Lys Asp
            180                 185
```

<210> SEQ ID NO 11
<211> LENGTH: 375
<212> TYPE: PRT
<213> ORGANISM: Homo sapiens

<400> SEQUENCE: 11

```
Met Glu Glu Glu Ile Ala Ala Leu Val Ile Asp Asn Gly Ser Gly Met
  1               5                  10                  15
Cys Lys Ala Gly Phe Ala Gly Asp Asp Ala Pro Arg Ala Val Phe Pro
             20                  25                  30
Ser Ile Val Gly Arg Pro Arg His Gln Gly Val Met Val Gly Met Gly
             35                  40                  45
Gln Lys Asp Ser Tyr Val Gly Asp Glu Ala Gln Ser Lys Arg Gly Ile
 50                  55                  60
Leu Thr Leu Lys Tyr Pro Ile Glu His Gly Ile Val Thr Asn Trp Asp
 65                  70                  75                  80
Asp Met Glu Lys Ile Trp His His Thr Phe Tyr Asn Glu Leu Arg Val
                 85                  90                  95
Ala Pro Glu Glu His Pro Val Leu Leu Thr Glu Ala Pro Leu Asn Pro
            100                 105                 110
Lys Ala Asn Arg Glu Lys Met Thr Gln Ile Met Phe Glu Thr Phe Asn
            115                 120                 125
Thr Pro Ala Met Tyr Val Ala Ile Gln Ala Val Leu Ser Leu Tyr Ala
130                 135                 140
Ser Gly Arg Thr Thr Gly Ile Val Met Asp Ser Gly Asp Gly Val Thr
145                 150                 155                 160
His Thr Val Pro Ile Tyr Glu Gly Tyr Ala Leu Pro His Ala Ile Leu
                165                 170                 175
Arg Leu Asp Leu Ala Gly Arg Asp Leu Thr Asp Tyr Leu Met Lys Ile
            180                 185                 190
Leu Thr Glu Arg Gly Tyr Ser Phe Thr Thr Thr Ala Glu Arg Glu Ile
            195                 200                 205
Val Arg Asp Ile Lys Glu Lys Leu Cys Tyr Val Ala Leu Asp Phe Glu
210                 215                 220
Gln Glu Met Ala Thr Ala Ala Ser Ser Ser Ser Leu Glu Lys Ser Tyr
225                 230                 235                 240
Glu Leu Pro Asp Gly Gln Val Ile Thr Ile Gly Asn Glu Arg Phe Arg
                245                 250                 255
Cys Pro Glu Ala Leu Phe Gln Pro Ser Phe Leu Gly Met Glu Ser Cys
            260                 265                 270
Gly Ile His Glu Thr Thr Phe Asn Ser Ile Met Lys Cys Asp Val Asp
            275                 280                 285
Ile Arg Lys Asp Leu Tyr Ala Asn Thr Val Leu Ser Gly Gly Thr Thr
290                 295                 300
Met Tyr Pro Gly Ile Ala Asp Arg Met Gln Lys Glu Ile Thr Ala Leu
305                 310                 315                 320
Ala Pro Ser Thr Met Lys Ile Lys Ile Ile Ala Pro Pro Glu Arg Lys
                325                 330                 335
Tyr Ser Val Trp Ile Gly Gly Ser Ile Leu Ala Ser Leu Ser Thr Phe
            340                 345                 350
Gln Gln Met Trp Ile Ser Lys Gln Glu Tyr Asp Glu Ser Gly Pro Ser
            355                 360                 365
Ile Val His Arg Lys Cys Phe
            370             375
```

<210> SEQ ID NO 12
<211> LENGTH: 284
<212> TYPE: PRT
<213> ORGANISM: Homo sapiens

<400> SEQUENCE: 12

```
Met Asp Ala Ile Lys Lys Met Gln Met Leu Lys Leu Asp Lys Glu
1               5                   10                  15

Asn Ala Ile Asp Arg Ala Glu Gln Ala Glu Asp Lys Lys Gln Ala
                20                  25                  30

Glu Asp Arg Cys Lys Gln Leu Glu Glu Glu Gln Ala Leu Gln Lys
            35                  40                  45

Lys Leu Lys Gly Thr Glu Asp Glu Val Glu Lys Tyr Ser Glu Ser Val
    50                  55                  60

Lys Glu Ala Gln Glu Lys Leu Glu Gln Ala Glu Lys Lys Ala Thr Asp
65                  70                  75                  80

Ala Glu Ala Asp Val Ala Ser Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Asn Arg Ala Met Lys Asp Glu Glu Lys Met Glu Leu Gln
    130                 135                 140

Glu Met Gln Leu Lys Glu Ala Lys His Ile Ala Glu Asp Ser Asp Arg
145                 150                 155                 160

Lys Tyr Glu Glu Val Ala Arg Lys Leu Val Ile Leu Glu Gly Glu Leu
                165                 170                 175

Glu Arg Ser Glu Glu Arg Ala Glu Val Ala Glu Ser Arg Ala Arg Gln
            180                 185                 190

Leu Glu Glu Glu Leu Arg Thr Met Asp Gln Ala Leu Lys Ser Leu Met
        195                 200                 205

Ala Ser Glu Glu Glu Tyr Ser Thr Lys Glu Asp Lys Tyr Glu Glu Glu
    210                 215                 220

Ile Lys Leu Leu Glu Glu Lys Leu Lys Glu Ala Glu Thr Arg Ala Glu
225                 230                 235                 240

Phe Ala Glu Arg Ser Val Ala Lys Leu Glu Lys Thr Ile Asp Asp Leu
                245                 250                 255

Glu Glu Thr Leu Ala Ser Ala Lys Glu Glu Asn Val Glu Ile His Gln
            260                 265                 270

Thr Leu Asp Gln Thr Leu Leu Glu Leu Asn Asn Leu
        275                 280
```

<210> SEQ ID NO 13
<211> LENGTH: 184
<212> TYPE: PRT
<213> ORGANISM: Homo sapiens

<400> SEQUENCE: 13

```
Thr Val Phe Trp Met Ser Phe Leu Asp Ala Leu Glu Thr Gly Tyr Gly
1               5                   10                  15

Lys Tyr Lys Asn Pro Tyr His Asn Gln Ile His Ala Ala Asp Val Thr
                20                  25                  30

Gln Thr Val His Cys Phe Leu Leu Arg Thr Gly Met Val His Cys Leu
            35                  40                  45

Ser Glu Ile Glu Leu Leu Ala Ile Ile Phe Ala Ala Ala Ile His Asp
        50                  55                  60

Tyr Glu His Thr Gly Thr Thr Asn Ser Phe His Ile Gln Thr Lys Ser
65                  70                  75                  80
```

```
Glu Cys Ala Ile Val Tyr Asn Asp Arg Ser Val Leu Glu Asn His His
                85                  90                  95

Ile Ser Ser Val Phe Arg Leu Met Gln Asp Asp Glu Met Asn Ile Phe
            100             105                 110

Ile Asn Leu Thr Lys Asp Glu Phe Val Glu Leu Arg Ala Leu Val Ile
        115             120                 125

Glu Met Val Leu Ala Thr Asp Met Ser Cys His Phe Gln Gln Val Lys
    130                 135                 140

Thr Met Lys Thr Ala Leu Gln Gln Leu Glu Arg Ile Asp Lys Ser Lys
145                 150                 155                 160

Ala Leu Ser Leu Leu Leu His Ala Ala Asp Ile Ser His Pro Thr Lys
            165                 170                 175

Gln Trp Leu Val His Ser Arg Trp
            180
```

TUMOR MARKERS FOR OVARIAN CANCER DIAGNOSIS

BACKGROUND OF THE INVENTION

1. Field of the Invention

The present invention relates to a tumor marker for diagnosis of cancer, especially for diagnosis of ovarian cancer, which can be applied in early diagnosis of ovarian cancer.

2. The Prior Arts

Human ovarian cancer is one of the common gynecological malignancies. In the developed country, it is one of the leading causes of death of the gynecological cancers, and the five-year survival rate is only about 30%. Overall about one woman in 70 will get ovarian cancer, and estimated one woman in 100 will die from this cancer in USA. This is because the illness is often diagnosed during late stage of the cancer. The cancer has often spread beyond the ovaries at that time, and therefore related to the low survival rate. Though Taiwanese women do not have a high incidence of ovarian cancer, but the incidence has increased over past two decades.

The five-year survival rate will up to 90-95 percent if the ovarian cancer is caught very early according to previous medical reports. The lack of reliable tumor marker has made the early detection of ovarian cancer difficult. Therefore most of the ovarian cancer patients will be diagnosed when the cancer cells have been spread. The survival rate thus cannot be lowered.

CA-125, cancer antigen-125, is a protein that may be released into the bloodstream, and is found at levels in most ovarian cancer cells. It is also a serum marker being studied thoroughly. The known detection method for ovarian cancer is the measurement of CA-125 in serum to assess the risk of having ovarian cancer.

The CA-125 test only returns a true positive result for about 50% of Stage I ovarian cancer patients though it has an 80% chance of returning true positive results from stage II, III, and IV ovarian cancer patients. It yields many false positive results. Therefore it is not recommended as a diagnostic tool or target for ovarian cancer in early stage cancers. Due to the current limitation to early diagnosis of ovarian cancer, it is important to search and identify new potential biomarkers in ovarian cancer.

SUMMARY OF THE INVENTION

In order to overcome the drawbacks of the prior art as described above, a primary object of the present invention is to provide an ovarian cancer marker to properly detect ovarian cancer at an early stage.

Another object of the present invention is to provide a method for the detection of ovarian cancer to identify ovarian cancer at an early stage.

To fulfill the objective of the present invention, a tumor marker for ovarian cancer diagnosis is selected from the group consisting of galectin-1 having the sequence of SEQ ID NO: 1, cathepsin B having the sequence of SEQ ID NO: 2, MHC class I antigen_having the sequence of SEQ ID NO: 3, heat shock protein 27 (HSP 27) having the sequence of SEQ ID NO: 4, ubiquitin carboxy-termal esterase L1 having the sequence of SEQ ID NO: 5, plasma retinol-binding protein (PRBP) having the sequence of SEQ ID NO: 6, transthyretin having the sequence of SEQ ID NO: 7, SH3 binding glutamate-rich protein having the sequence of SEQ ID NO: 8, tubulin-specific chaperone A having the sequence of SEQ ID NO: 9, RNA binding protein regulatory subunit having the sequence of SEQ ID NO: 10, γ-actin having the sequence of SEQ ID NO: 11, tropomyosin having the sequence of SEQ ID NO: 12 and calcium/calmodulin-stimulated cyclic nucleotide phosphatase having the sequence of SEQ ID NO: 13.

Compared with non-cancerous ovarian tissue (normal ovarian tissue), the cancer marker of the present invention is either up-regulated or down-regulated in ovarian tissues from ovarian cancer patients.

In addition, a method for detecting ovarian cancer according to the present invention comprises the steps of:

(1) obtaining an ovarian tissue sample from an individual to be diagnosed and an ovarian tissue sample from a non-cancerous ovarian tissue;

(2) determining expression level of a tumor marker having an amino acid sequence selected from the group consisting of SEQ ID NOs: 1-13 in the ovarian tissue samples of the individual to be diagnosed and the non-cancerous ovarian tissue respectively;

(3) comparing the expression levels of the tumor markers having the same amino acid sequence in the ovarian tissue samples of step (2); and (4) determining if the individual being diagnosed is affected with the ovarian cancer or not from the result of step (3), wherein at least one of the tumor markers having the amino acid sequences of SEQ ID NOs: 1-5 is up-regulated and/or at least one of the tumor markers having the amino acid sequences of SEQ ID NOs: 6-13 is down-regulated in the ovarian tissue samples of the individual being diagnosed in comparison with the non-cancerous ovarian tissue indicating the presence of the ovarian cancer.

The tumor markers according to the present invention can be applied as a diagnostic tool in detecting ovarian cancer at an early stage. In addition, the detection method for the diagnosis of ovarian cancer according to the present invention can also be applied in detecting ovarian cancer at an early stage.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

Figure 1:
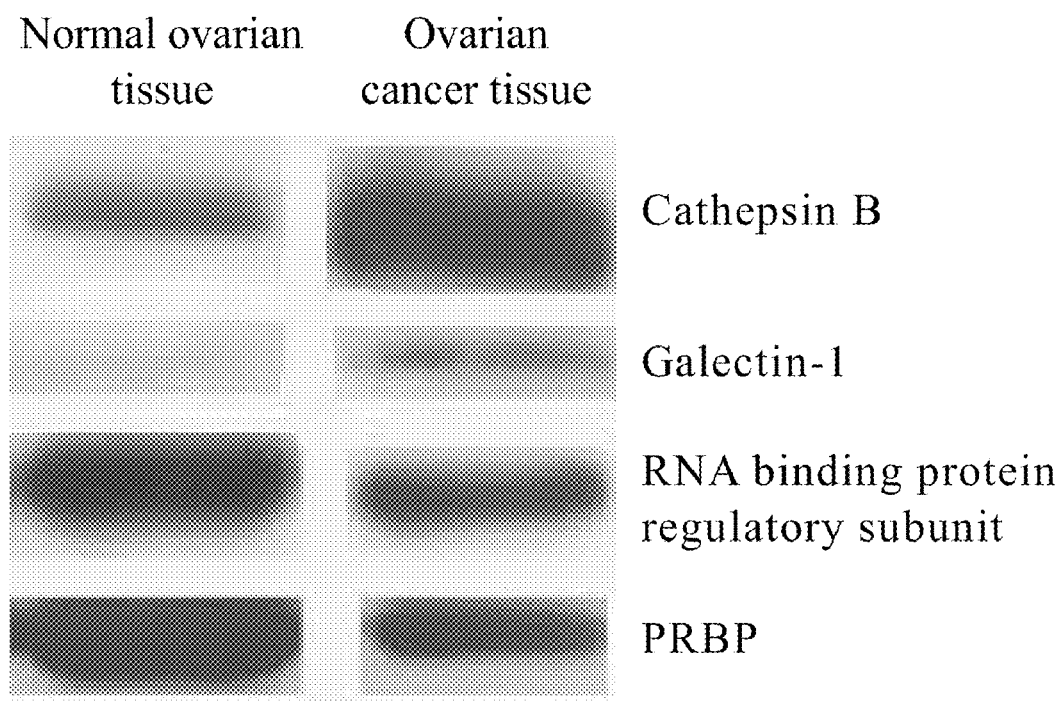
FIG. 1 shows Western blot analysis of cathepsin B, galectin-1, RNA binding protein regulatory subunit, and plasma retinol-binding protein (PRBP) from normal ovarian tissue and ovarian cancer tissue samples.

The tumor marker of the present invention can be applied in early diagnosis of ovarian cancer. Compared with normal ovarian tissues, the expression level of tumor marker according to the present invention is either up-regulated or down-regulated in ovarian tissue of ovarian cancer patient. Following comparison between tumor tissues and corresponding normal tissues, the examples for up-regulated tumor marker are galectin-1 (SEQ ID NO. 1), cathepsin B (SEQ ID NO. 2), MHC class I antigen (SEQ ID NO. 3), heat shock protein (HSP) 27 (SEQ ID NO. 4) and ubiquitin carboxy-termal esterase L1 (SEQ ID NO. 5). On the contrary, the examples for down-regulated tumor marker are plasma retinol-binding protein (PRBP) (SEQ ID NO. 6), transthyretin (SEQ ID NO. 7), SH3 binding glutamate-rich protein (SEQ ID NO. 8), tubulin-specific chaperone A (SEQ ID NO. 9), RNA binding protein regulatory subunit (SEQ ID NO. 10), γ-actin (SEQ ID NO. 11), tropomyosin (SEQ ID NO. 12) and calcium/calmodulin-stimulated cyclic nucleotide phosphatase (SEQ ID NO. 13).

The changes of expression level of the tumor marker in the ovarian tissues according to the present invention can be easily determined with the relevant known protein analysis techniques, which include but are not limited to polyacrylamide gel electrophoresis (PAGE), Western blot, Dot blot and so on, by the person skilled in the art after reading the disclosure of the specification. A Example for polyacrylamide gel electrophoresis include but is not limited to sodium dodecyl sulfate polyacrylamide gel electrophoresis (SDS-PAGE).

When the expression levels of the tumor markers in the ovarian tissues according to the present invention were analyzed with PAGE combined with ImageMaster™ 2D Elite, the preferred ratio of signal strength for up-regulated protein dots (tumor markers) in the gel slabs after gel electrophoresis is larger or equal to 1.25 (ovarian cancer samples in comparison with normal ovarian tissues); and the preferred ratio of signal strength for down-regulated protein dot (tumor markers) in the gel slabs is smaller or equal to 0.8 (ovarian cancer samples in comparison with normal ovarian tissues). The gel slabs after gel electrophoresis were stained with Silver staining solution or Coomassie Brilliant Blue staining solution.

The present invention also provides a method for the detection of ovarian cancer to identify ovarian cancer at an early stage since the expression levels of the tumor markers in the ovarian tissues will be changed in accordance with the invasion of tumor cells. The method for detecting ovarian cancer according to the invention first obtains an ovarian tissue sample from an individual to be diagnosed and an ovarian tissue sample from a non-cancerous ovarian tissue (normal ovarian tissue); and then determining expression level of a tumor marker having an amino acid sequence selected from the group consisting of SEQ ID NOs: 1-13 in the ovarian tissue samples of the individual to be diagnosed and the non-cancerous ovarian tissue respectively through the known methods. Then the expression levels of the tumor markers having the same amino acid sequence in the ovarian tissue samples of the individual to be diagnosed and of the non-cancerous ovarian tissue are compared with each other. Lastly, comparison result of the expression levels of tumor markers is used to determine whether the expression level has been changed (up-regulated or down-regulated), and to identify if the individual being diagnosed is affected with the ovarian cancer or not, wherein at least one of the tumor markers having the amino acid sequences of SEQ ID NOs: 1-5 is up-regulated and/or at least one of the tumor markers having the amino acid sequences of SEQ ID NOs: 6-13 is down-regulated in the ovarian tissue samples of the individual being diagnosed in comparison with the non-cancerous ovarian tissue indicating the presence of the ovarian cancer.

The abovementioned non-cancerous ovarian tissue (normal ovarian tissue) could be obtained from other individual, who is not being affected by the ovarian cancer; or other parts of the ovarian tissue sample to be diagnosed, which is not invaded by the cancer, in the same individual.

The abovementioned method to analyze the expression levels of the tumor markers can be easily performed with the relevant known protein analysis techniques, which include but are not limited to polyacrylamide gel electrophoresis (PAGE), Western blot, Dot blot and so on, by the person skilled in the art after reading the disclosure of the specification. Examples for polyacrylamide gel electrophoresis include but are not limited to sodium dodecyl sulfate polyacrylamide gel electrophoresis (SDS-PAGE).

The abovementioned expression level changes of the tumor markers can be up-regulated or down-regulated. For example, PAGE combined with ImageMaster™ 2D Elite is used to analyze the expression levels of the tumor markers in the ovarian tissues according to the present invention. When the ratio of signal strength for up-regulated protein dots (tumor markers) in the gel slabs after gel electrophoresis is larger or equal to 1.25 (ovarian cancer samples in comparison with normal ovarian tissues); or the ratio of signal strength for down-regulated protein dot (tumor markers) in the gel slabs is smaller or equal to 0.8 (ovarian cancer samples in comparison with normal ovarian tissues), the individual is identified to be affected with ovarian cancer. On the contrary, the individual is identified not to be affected with ovarian cancer if the signal ratio is within the abovementioned value range.

The abovementioned ovarian cancer comprises clinical stage I, II, III, and IV ovarian cancer.

In addition, the accuracy of diagnosis of ovarian cancers performed with the method of the present invention can be increased through combining the analysis results of the expression levels from multiple of the tumor markers.

Example 1

Screening of Tumor Markers

The ovarian tissues collected in the present invention comprised of 36 epithelial ovarian cancers, 10 borderline malignancies and 18 normal ovaries. Clinical and histological characteristics of these 36 ovarian cancer tissue samples are summarized in Table 1.

The histologic subtypes of ovarian cancer include clear cell, endometrioid, mucinous, serous and others as shown in Table 1. Among these 36 ovarian cancer tissue samples, 10 were of clinical stage I, 6 of clinical stage II, 18 of clinical stage III, and 2 of clinical stage IV.

Protein extracts from the normal ovarian tissues and the ovarian cancer tissues were separated on SDS-PAGE followed by 2D-polyacrylamide gel electrophoresis.

2D-polyacrylamide gel electrophoresis was performed on a 130 mm, linear immobilized pH 4-7 Immobiline DryStrip (Amersham Pharmacia Biotech, Piscataway, N.J., USA) using MULTIPHOR II Electrophoresis system. The ovarian tissues were frozen in liquid nitrogen and grinded to a fine powder. The powder was extracted with an extract buffer containing phosphate buffered saline (PBS) buffer and protease inhibitor. The supernatant was precipitated with trichloroacetic acid (TCA) to final concentration of 5% after extraction solution was centrifuged. The precipitated pellet was resuspended in buffer containing 8 M urea and 0.1 M dithiothreitol (DTT).

Portions of 450 µg of samples were rehydrated overnight at room temperature. After rehydration, the gel electrophoresis was carried out at 400 V for 1 h, followed by a linear gradient from 400 V to 3500 V for 1.5 h, and fixed at 3500 V for a total of 70 kVh. Prior to the second-dimension separation, the Immobiline DryStrips were pre-equilibrated with equilibration buffer containing 0.05 M Tris-HCl (pH 8.8), 6 M urea, 2% (w/v) sodium dodecyl sulfate (SDS), 30% (v/v) glycerol, and 1% (w/v) dithiothreitol for 15 min. Then the strips were re-equilibrated in the same equilibration buffer but replacing dithiothreitol with 2.5% (w/v) iodoacetamide for 15 min. For the second-dimension separation, the serum proteins were separated in a 12.5% polyacrylamide gel in running buffer containing 0.025 M Tris pH 8.8, 0.192 M Glycine and 0.1% SDS. The second dimension gels were electrophoresed at constant current 10 mA through the stacking gel and at 20 mA through the separating gel.

The gel slabs were stained by the Silver stain method or with Coomassie Blue solution containing 0.25% (w/v) Coomassie Brilliant Blue R 250, 35% (v/v) methanol, and 7% (v/v) acetic acid. Then each gel was de-stained with 35% methanol/7% acetic acid.

Protein spots in gel slabs were different in intensity after staining. Proteins in high levels generate deep color (high intensity), while low levels generate light color (low intensity). The protein band intensities of the cancer tissue and normal tissues in the gel slabs were compared. And 13 protein spots were selected from 2D gels as representative protein spots among normal ovaries, borderline serous ovarian tumors and invasive ovarian carcinomas. Selected protein spots from 2D gels were excised, double distilled water (ddH$_2$O) washed, and destained with 0.025 M ammonium bicarbonate/50% acetonitrile (ACN). The protein in the protein spot was digested overnight with trypsin at 37° C., and the proteolytic peptide fragments were extracted with 1% Trifluoroacetic acid (TFA)/50% ACN. After lyophilized, the extracted peptides were dissolved in 30% ACN and mixed with matrix solution, then subjected to matrix assisted laser desorption ionization time-of-flight mass spectrometry (MALDI-TOF MS) analysis.

MALDI mass spectra were obtained using an Autoflex workstation (Bruker-Daltonics, Bremen, Germany) equipped with a 337-nm wavelength nitrogen laser. The peptide spectra, acquired in reflection mode at an accelerating voltage of 20 kV, were the sum of 50 laser shots. The mass spectra were externally calibrated using low mass peptide standards. This procedure typically results in mass accuracies of 50-100 ppm. The de-isotope tryptic peptide fragments were used for protein identification by using the MASCOT search engine based on the peptide mass fingerprinting of entire NCBI and SwissPort protein databases.

Thirteen protein spots identified through entire NCBI and SwissPort protein databases, were galectin-1 having the sequence of SEQ ID NO: 1 (sequence version 2), cathepsin B having the sequence of SEQ ID NO: 2 (sequence version 0), MHC class I antigen having the sequence of SEQ ID NO: 3 (sequence version 1), heat shock protein 27 (HSP 27) having the sequence of SEQ ID NO: 4 (sequence version 1), ubiquitin carboxy-termal esterase L1 having the sequence of SEQ ID NO: 5 (sequence version 2), plasma retinol-binding protein (PRBP) having the sequence of SEQ ID NO: 6 (sequence version 1), transthyretin having the sequence of SEQ ID NO: 7 (sequence version 1), SH3 binding glutamate-rich protein having the sequence of SEQ ID NO: 8 (sequence version 0), tubulin-specific chaperone A having the sequence of SEQ ID NO: 9 (sequence version 1), RNA binding protein regulatory subunit having the sequence of SEQ ID NO: 10 (sequence version 1), γ-actin having the sequence of SEQ ID NO: 11 (sequence version 1), tropomyosin having the sequence of SEQ ID NO: 12 (sequence version 1) and calcium/calmodulin-stimulated cyclic nucleotide phosphatase having the sequence of SEQ ID NO: 13 (sequence version 1). Characterization of these 13 protein spots was listed in Table 2.

On the other hand, signal strengths of the Silver-stained gel slabs were detected with ImageMaster™ 2D Elite software (Amersham Biosciences biotech, N.J., USA) to analyze the differential expression of protein spots in 2D-gal electrophoresis among normal, borderline and malignant ovarian tissues, and the results were shown in Table 3.

ImageMaster™ 2D Elite result from Table 3 showed that galectin-1, cathepsin B, MHC class I antigen, HSP 27 and ubiquitin carboxy-termal esterase L1 were up-regulated (signal strength≧1.25 as compared with normal ovarian tissue) in ovarian cancer tissues; while CRBP, transthyretin, SH3 binding glutamate-rich protein, tubulin-specific chaperone A, RNA binding protein regulatory subunit, γ-actin, tropomyosin and calcium/calmodulin-stimulated cyclic nucleotide phosphatase were down-regulated (signal strength≦0.80 as compared with normal tissue).

Example 2

Four of the protein spots detected in 2D-gel electrophoresis images, which included: cathepsin B, galectin-1, RNA-binding protein regulatory subunit, and plasma retinol-binding protein (PRBP), were further identified through Dot blot, or SDS-PAGE followed by Western blotting analyses.

The tissues from normal or cancer ovaries were grinded with plastic pestles in ¼ PBS buffer containing protease inhibitor cocktail (Calbiochem). After centrifugation 15,000×g for 10 min at 4° C., the supernatant was transferred to an eppendorf tube and subjected to Dot blot, or SDS-PAGE followed by Western blotting analyses. The protein concentration was determined by the absorption of $A_{280}$.

For SDS-PAGE analysis, 30 μg of protein sample was applied to each lane. All samples were heated for 5 min at 95° C. before loading into the 15% polyacrylamide gel. After electrophoresis, proteins were electroblotted onto polyvinylidene difluoride (PVDF) membrane. For Dot blot analysis, 5 μg of protein was loaded onto PVDF membrane directly. The membranes were blocked in a blocking solution (5% nonfat dried milk in 1×PBS with 2% Tween-20) for 1 hr at room temperature. The membranes were then probed with anti-retinol binding protein antibody (USBiological, Cat# R1701-16), anti-cathepsin B antibody (USBiological, Cat# C2097-03D), anti-PARK7 antibody (USBiological, Cat# P3111), and anti-galectin-1 antibody (Novocastra, Cat# NCL-GAL1) in blocking solution for 2 hr at room temperature. After washing with the PBST solution (0.05% Tween-20 in 1×PBS), the membranes were incubated with horseradish peroxidase-conjugated anti-immunoglobulin antibody in the blocking solution for 1 hr at room temperature. After additional wash with the PBST solution, membranes were developed with Western Lightning Chemiluminescence Reagent Plus (PerkinElmer). The membranes were scanned using an UMAX Astra 4000U scanner to detect the signals. The signal strengths from Dot blot were quantified with a GenePix 6.0 software (Table 4), and the images from Western blotting were analyzed with a Fujifilm Science Lab 98 software (Image Gauge V3.12) (FIG. 1).

Results from Table 4 and FIG. 1 showed that both cathepsin B and galectin-1 were up-regulated, while RNA binding protein regulatory subunit and plasma retinol-binding protein (PRBP) were down-regulated in the ovarian cancer tissue samples. These results are in accordance with Example 1.

TABLE 1

Clinical and histologic characteristics of ovarian cancer tissue samples.

| No. | Age | Histologic type | Stage | Grade of Differentiation* |
|---|---|---|---|---|
| 1 | 43 | Clear cell carcinoma | Ia | III |
| 2 | 45 | Clear cell carcinoma | Ia | III |
| 3 | 48 | Clear cell carcinoma | Ia | III |
| 4 | 43 | Clear cell carcinoma | Ib | III |
| 5 | 52 | Clear cell carcinoma | Ic | III |
| 6 | 48 | Endometrioid adenocarcinoma | Ia | I |
| 7 | 81 | Endometrioid adenocarcinoma | Ia | I |
| 8 | 46 | Endometrioid adenocarcinoma | Ic | I |
| 9 | 48 | Mucinous cystadenocarcinoma | Ia | I |
| 10 | 36 | Mucinous cystadenocarcinoma | Ia | II |
| 11 | 65 | Serous papillary adenoarcinoma | II | II |
| 12 | 41 | Serous cyadenocarcinoma | IIa | III |
| 13 | 56 | Serous adenocarcinoma | IIa | III |
| 14 | 56 | Serous carcinoma | IIa | II |
| 15 | 70 | Serous cystadenocarcinoma | IIb | II |
| 16 | 59 | Endometrioid adenocarcinoma | IIa | I |
| 17 | 62 | Serous cystadenocarcinoma | III | III |
| 18 | 54 | Serous papillary adenoarcinoma | III | III |
| 19 | 61 | Squamous cell carcinoma | IIIa | III |
| 20 | 58 | Clear cell carcinoma | IIIc | III |
| 21 | 60 | Clear cell carcinoma | IIIc | III |
| 22 | 46 | Endometrioid adenocarcinoma | IIIb | I |
| 23 | 44 | Endometrioid adenocarcinoma | IIIc | III |
| 24 | 56 | Serous carcinoma | IIIb | III |
| 25 | 61 | Serous cystadenocarcinoma | IIIc | II |
| 26 | 70 | Serous papillary adenoarcinoma | IIIb | II |
| 27 | 78 | Serous papillary adenoarcinoma | IIIb | III |
| 28 | 42 | Serous papillary adenoarcinoma | IIIc | II |
| 29 | 70 | Serous papillary adenoarcinoma | IIIc | II |
| 30 | 46 | Serous papillary adenoarcinoma | IIIc | II |
| 31 | 82 | Serous papillary adenoarcinoma | IIIc | III |
| 32 | 72 | Serous papillary adenoarcinoma | IIIc | III |
| 33 | 71 | Serous surface papillary adenocarcinoma | IIIb | II |
| 34 | 59 | Serous surface papillary adenocarcinoma | IIIc | III |
| 35 | 47 | Mixed adenocarcinoma (Endometrioid & Serous) | IV | III |
| 36 | 51 | Serous cystadenocarcinoma | IV | III |

*Differentiation: Grade I, well differentiation; Grade II, moderate differentiation; Grade III, poor differentiation.

TABLE 2

List of protein spots demonostrating differential expression in 2D-gel electrophoresis among different types of ovarian tissues in this study

| Sequence ID No. | Protein Name | Acession Number | PI | M.W. |
|---|---|---|---|---|
| 1 | Galectin-1 | P09382 | 5.33 | 14715.70 |
| 2 | Cathepsin B | 2007265A | 5.44 | 17154.04 |
| 3 | MHC class I antigen | CAI40345 | 6.33 | 21230.37 |
| 4 | HSP 27 | BAB17232 | 5.98 | 22782.52 |
| 5 | Ubiquitin carboxyl-terminal esterase L1 | NP_004172 | 5.33 | 24824.34 |
| 6 | Plasma retinol-binding protein | P02753 | 5.76 | 23044.0 |
| 7 | Transthyretin | P02766 | 5.52 | 15887.0 |
| 8 | SH3 binding glutamate-rich protein | JE0178 | 5.22 | 12774.25 |
| 9 | Tubulin-specific chaperone A | AAP36018 | 5.25 | 12854.83 |
| 10 | RNA-binding protein regulatory subunit | AAH08188 | 6.33 | 19891.05 |
| 11 | γ-Actin | P63261 | 5.31 | 41792.8 |
| 12 | Tropomyosin | AAB59509 | 4.63 | 32989.81 |
| 13 | Calcium/calmodulin-stimulated cyclic nucleotide phosphatase | AAB50018 | 6.07 | 21246.42 |

TABLE 3

Analysis of signal strengths of differential expression of protein spots in 2D-gel electrophoresis maps among normal, borderline and malignant ovarian tissue.

| Sequence ID No. | Protein names | Types of tissue samples | | |
|---|---|---|---|---|
| | | Normal (n = 18) | Borderline (n = 10) | Malignant (n = 36) |
| 1 | Galectin-1 | 1.00 ± 0.54 | 0.49 ± 0.29 | 1.34 ± 1.01 |
| 2 | Cathepsin B | 1.00 ± 0.20 | 0.60 ± 0.54 | 1.43 ± 1.09 |
| 3 | MHC class I antigen | 1.00 ± 0.30 | 1.17 ± 0.57 | 1.48 ± 0.85 |
| 4 | HSP 27 | 1.00 ± 0.35 | 1.25 ± 0.50 | 1.31 ± 0.66 |
| 5 | Ubiquitin carboxyl-terminal esterase L1 | 1.00 ± 0.33 | 1.49 ± 0.54 | 1.27 ± 0.44 |
| 6 | Plasma retinol-binding protein | 1.00 ± 0.56 | 0.51 ± 0.87 | 0.25 ± 0.35 |
| 7 | Transthyretin | 1.00 ± 0.70 | 0.86 ± 0.78 | 0.74 ± 0.76 |
| 8 | SH3 binding glutamate-rich protein | 1.00 ± 0.72 | 0.42 ± 0.45 | 0.62 ± 0.54 |
| 9 | Tubulin-specific chaperone A | 1.00 ± 0.41 | 1.25 ± 1.68 | 0.68 ± 1.08 |
| 10 | RNA-binding protein regulatory subunit | 1.00 ± 0.75 | 0.57 ± 0.43 | 0.74 ± 0.61 |
| 11 | γ-Actin | 1.00 ± 0.33 | 0.21 ± 0.11 | 0.15 ± 0.09 |
| 12 | Tropomyosin | 1.00 ± 0.30 | 0.89 ± 0.41 | 0.78 ± 0.38 |
| 13 | Calcium/calmodulin-stimulated cyclic nucleotide phosphatase | 1.00 ± 0.31 | 0.88 ± 0.36 | 0.75 ± 0.29 |

TABLE 4

Dot blot analysis of expression of cathepsin B, galectin-1, RNA-binding protein regulatory subunit and CRBP in different stages of ovarian cancer and borderline tissues compared with normal ovary tissues.

| Proteins | Tissue types and Stage | Signal Strength [a] | Ratio |
|---|---|---|---|
| Cathepsin B | Borderline | 373687.2 ± 177135.2 | 2.99 [b] |
| | I + II | 374300.8 ± 108412.8 | 2.99 [b] |
| | III | 378754.6 ± 125816.2 | 3.03 [b] |
| | I~III | 376775.1 ± 115001.0 | 3.01 [b] |
| | Normal | 125072.3 ± 79980.6 | |
| Galectin-1 | Borderline | 9813.2 ± 2655.1 | 1.04 |
| | I + II | 10276.0 ± 4532.7 | 1.09 |
| | III | 15073.8 ± 4235.9 | 1.60 [b] |
| | I~III | 12941.4 ± 4896.6 | 1.38 [b] |
| | Normal | 9401.0 ± 4230.3 | |
| RNA-binding protein regulatory subunit | Borderline | 12539.6 ± 2948.0 | 0.63 [b] |
| | I + II | 16127.6 ± 4705.3 | 0.81 [b] |
| | III | 15510.5 ± 3127.5 | 0.78 [b] |
| | I~III | 15770.4 ± 3760.6 | 0.79 [b] |
| | Normal | 19857.9 ± 4074.0 | |
| Plasma retinol-binding protein | Borderline | 6828.1 ± 4850.8 | 0.54 [b] |
| | I + II | 4813.1 ± 3298.0 | 0.38 [b] |
| | III | 10771.5 ± 7667.6 | 0.84 |
| | I~III | 8744.7 ± 6806.3 | 0.69 [b] |
| | Normal | 12748.8 ± 4763.9 | |

[a] Each value represents a mean ± S.D. Borderline (n = 10), stage I + II (n = 8), stage III (n = 11), normal ovary (n = 20).
[b] $P < 0.05$, compared with normal.

What is claimed is:

1. A method for detecting ovarian cancer, which comprises the steps of:
   (1) obtaining an ovarian tissue sample from an individual to be diagnosed and an ovarian tissue sample from a non-cancerous ovarian tissue;
   (2) determining expression levels of thirteen tumor markers having the amino acid sequences of SEQ ID NOs: 1-13 in the ovarian tissue sample of the individual to be diagnosed and the non-cancerous ovarian tissue sample;
   (3) comparing the expression level of each tumor marker in the ovarian tissue sample of the individual to be diagnosed to the expression level of the corresponding tumor marker in the non-cancerous ovarian tissue sample; and
   (4) determining that the individual being diagnosed is affected with ovarian cancer if the tumor markers having the amino acid sequences of SEQ ID NOs: 1-5 are up-regulated and the tumor markers having the amino acid sequences of SEQ ID NOs: 6-13 are down-regulated in the ovarian tissue sample of the individual being diagnosed in comparison with the non-cancerous ovarian tissue sample.

2. The method of claim 1, wherein the expression levels of the tumor markers are determined by gel electrophoresis.

3. The method of claim 1, wherein the expression levels of the tumor markers are determined by Western Blot.

4. The method of claim 1, wherein the expression levels of the tumor markers are determined by Dot blot.

5. The method of claim 1, wherein the non-cancerous ovarian tissue sample is obtained from the same individual to be diagnosed.

6. The method of claim 1, wherein the ovarian cancer is stage I, II, III, or IV ovarian cancer.

* * * * *